(12) United States Patent
Chern et al.

(10) Patent No.: US 7,897,764 B2
(45) Date of Patent: Mar. 1, 2011

(54) THIOUREA DERIVATIVES

(75) Inventors: Jyh-Haur Chern, Taipei (TW); Tsu-An Hsu, Taipei (TW); Iou-Jiun Kang, Wandan Township (TW); Li-Wen Wang, Kaohsiung (TW); Chung-Chi Lee, Chung-He (TW); Yen-Chun Lee, Taitung (TW); Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 18 days.

(21) Appl. No.: 12/115,221

(22) Filed: May 5, 2008

(65) Prior Publication Data

US 2008/0306090 A1 Dec. 11, 2008

Related U.S. Application Data

(60) Provisional application No. 60/942,808, filed on Jun. 8, 2007.

(51) Int. Cl.
*C07D 241/04* (2006.01)
*C07D 295/00* (2006.01)

(52) U.S. Cl. .......... 544/392; 544/395; 544/396

(58) Field of Classification Search .......... 544/395, 544/396
See application file for complete search history.

(56) References Cited

U.S. PATENT DOCUMENTS

| | | | |
|---|---|---|---|
| 3,890,348 A | 6/1975 | Kathawala | |
| 4,221,817 A | 9/1980 | Tenne | |
| 4,413,006 A * | 11/1983 | Kanno et al. ........... | 514/255.03 |
| 4,574,124 A | 3/1986 | Kabbe et al. | |
| 5,932,742 A | 8/1999 | Yoon et al. | |
| 6,696,487 B2 | 2/2004 | Gerusz et al. | |
| 6,706,751 B2 | 3/2004 | Aebi et al. | |
| 7,094,807 B2 | 8/2006 | Chen et al. | |
| 7,102,007 B2 | 9/2006 | Aebi et al. | |
| 2005/0020624 A1 | 1/2005 | Aebi et al. | |
| 2005/0032849 A1 | 2/2005 | Phadke et al. | |
| 2005/0228013 A1 | 10/2005 | Thurkauf et al. | |
| 2006/0025416 A1 | 2/2006 | Phadke et al. | |
| 2009/0264404 A1 * | 10/2009 | Yamashita et al. ..... | 514/210.18 |

FOREIGN PATENT DOCUMENTS

| | | | |
|---|---|---|---|
| DE | 2040438 | * | 3/1971 |
| FR | 2 447 378 | * | 1/1979 |
| GB | 1 332 008 | * | 10/1973 |
| GB | 2 056 968 | * | 3/1981 |
| JP | 2005330284 | | 2/2005 |
| JP | 2005/144790 | | 5/2005 |
| WO | WO 99/40088 | | 8/1999 |
| WO | WO2004/046095 | | 6/2004 |
| WO | WO2004/096210 | | 11/2004 |
| WO | WO 2005/095345 | | 10/2005 |
| WO | WO2006/122011 | | 11/2006 |

OTHER PUBLICATIONS

Cory et al., "Use of an Aqueous Soluble Tetrazolium/Formazan Assay for Cell Growth Assays in Culture," *Cancer Communications*, vol. 3, No. 7, (1991).
Honda et al., Chem. Abst. 135 357776 (2001).
Willson et al. Chem. Abst. 118: 212577 (1993).
Bennett et al., J. Am Chem Soc. 1953 75(23); 6039-6040.
Gugliamelli, Luis et al., Anales de la Asociacion Quimica Argentina (1927), 15, pp. 337-362.
Arafa, Reem et al., J. Med. Chem. 2005, 48, 5480-5488.
Document No. 142:56122, retrieved from CAPLUS on Jan. 6, 2010.
Document No. 140:209908, retrieved from CAPLUS on Jan. 6, 2010.
Document No. 86:55235, retrieved from CAPLUS on Jan. 6, 2010.
Document No. 140:406359, retrieved from CAPLUS on Jan. 6, 2010.
Document No. 143:163157, retrieved from CAPLUS on Jan. 6, 2010.
Document No. 139:69296, retrieved from CAPLUS on Jan. 6, 2010.
Document No. 132:279477, retrieved from CAPLUS on Jan. 6, 2010.

* cited by examiner

*Primary Examiner* — James O Wilson
*Assistant Examiner* — Erich A Leeser
(74) *Attorney, Agent, or Firm* — Occhiuti Rohlicek & Tsao LLP

(57) ABSTRACT

Thiourea compounds of the following formula:

$$H_2N-\overset{X}{\underset{\underset{R_1}{|}}{C}}-N-A_1-Y-\overset{R_2}{\underset{\underset{}{|}}{C}}\overset{R_3}{\underset{\underset{}{|}}{C}}_n-Z-A_2,$$

wherein n, $R_1$, $R_2$, $R_3$, $A_1$, $A_2$, X, Y, and Z are defined herein. Also disclosed is a method of treating hepatitis C virus infection with these compounds.

6 Claims, No Drawings

THIOUREA DERIVATIVES

CROSS REFERENCE TO RELATED APPLICATIONS

This application claims priority to U.S. Provisional Application Ser. No. 60/942,808 filed Jun. 8, 2007. The contents of the prior application are hereby incorporated by reference in their entireties.

BACKGROUND

Hepatitis C virus (HCV) infection is estimated to affect 170 million individuals worldwide. This disease is primarily transmitted through contaminated blood products. Although its spread has been slowed as a result of improvement in blood screening in many countries, it remains the leading cause of liver disease-related deaths in the world. For example, it causes about 10,000 deaths annually in the U.S. alone. In the absence of effective therapies, the death rate is expected to triple over the next 2 decades.

Current treatments based on interferon-alpha have low success rates, particularly for genotype-1 infections predominant in Europe, Japan, and the U.S. Also, they are expensive and poorly received by patients. Thus, there is a need to develop better therapeutic agents for treating HCV infection.

SUMMARY

This invention is based on the discovery that certain thiourea compounds are effective in treating hepatitis C virus infection.

In one aspect, this invention relates to a compound of formula (I):

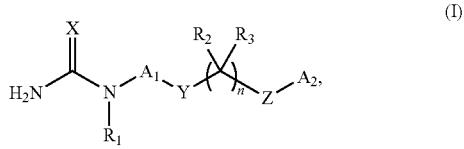

in which n is 1-10; $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl; each of $R_2$ and $R_3$, independently, is H, halo, nitro, cyano, amino, hydroxy, alkoxy, aryloxy, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl; $A_1$ is arylene or heteroarylene, optionally substituted with halo, nitro, cyano, amino, hydroxy, alkoxy, aryloxy, alkylcarbonyl, alkoxycarbonyl, carboxy, aminocarbonyl, carbonylamino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl; $A_2$ is alkyl, clycloalkyl, heterocycloalkyl, aryl, or heteroaryl, in which alkyl is optionally substituted with halo, nitro, cyano, amino, hydroxy, alkoxy, aryloxy, alkylcarbonyl, alkoxycarbonyl, carboxy, aminocarbonyl, carbonylamino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl; and each of clycloalkyl, heterocycloalkyl, aryl, and heteroaryl is optionally substituted with halo, nitro, cyano, amino, hydroxy, alkoxy, aryloxy, alkylcarbonyl, alkoxycarbonyl, carboxy, aminocarbonyl, carbonylamino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl, or optionally fused with $C_3$-$C_{20}$ cycloalkyl, $C_3$-$C_{20}$ heterocycloalkyl, aryl, or heteroaryl; each of X and Y, independently, is O, S, or N($R_a$), in which $R_a$ is H, $C_1$-$C_{10}$ alkyl, $C_3$-$C_{20}$ cycloalkyl, $C_3$-$C_{20}$ heterocycloalkyl, aryl, or heteroaryl; and Z is —NHSO$_2$—, —NHC(=O)—, —C(=O)NH—, —NHC(=O)O—, —NHC(=O)NH—, —NHC(=S)NH—, —NHC(=NH)NH—, $C_3$-$C_{20}$ cycloalkyl, or $C_3$-$C_{20}$ heterocycloalkyl.

Referring to the above formula, some compounds of this invention have one or more of the following features: each of $R_1$, $R_2$, and $R_3$ is H; n is 5, 6, 7, or 8; X is S; Y is O; Z is —NHC(=S)NH—, —NHSO$_2$—, —NHC(=O)—, —C(=O)NH—, or

$A_1$ is phenylene (e.g., 1,3-phenylene or 1,4-phenylene); and $A_2$ is phenyl or naphthyl, optionally substituted with halo, alkoxy, aryloxy, $C_1$-$C_{10}$ alkyl, $C_3$-$C_{20}$ cycloalkyl, aryl, or heteroaryl, or fused with $C_3$-$C_{20}$ cycloalkyl, $C_3$-$C_{20}$ heterocycloalkyl, or heteroaryl.

The term "alkyl" refers to a monovalent or bivalent straight or branched hydrocarbon, containing 1-10 carbon atoms. Examples of alkyl include, but are not limited to, methyl, methylene, ethyl, ethylene, n-propyl, i-propyl, n-butyl, i-butyl, and t-butyl. The term "alkenyl" refers to a monovalent or bivalent straight or branched hydrocarbon containing 2-10 carbon atoms and one or more double bonds. Examples of alkenyl, but are not limited to, include ethenyl, propenyl, allyl, and 1,4-butadienyl. The term "alkynyl" refers to a monovalent or bivalent straight or branched hydrocarbon containing 2-10 carbon atoms and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy.

The term "cycloalkyl" refers to a monovalent or bivalent saturated hydrocarbon ring system having 3 to 12 carbon atoms. Examples of cycloalkyl include, but are not limited to, cyclopropyl, cyclobutyl, cyclopentyl, cyclopentenyl, cyclohexyl, cyclohexenyl, cycloheptyl, and cyclooctyl. The term "cycloalkenyl" refers to a monovalent or bivalent non-aromatic hydrocarbon ring system having 3 to 12 carbons and one or more double bonds. Examples include cyclopentanyl, cyclohexanyl, and cycloheptanyl. The term "heterocycloalkyl" refers to a monovalent or bivalent nonaromatic 5-8 membered monocyclic, 8-12 membered bicyclic, or 11-14 membered tricyclic ring system having one or more heteroatoms (such as O, N, S, or Se). Examples of heterocyclyl groups include, but are not limited to, piperazinyl, pyrrolidinyl, dioxanyl, morpholinyl, and tetrahydrofuranyl. The term "heterocycloalkenyl" refers to a nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, biphenyl, naphthyl, and anthracenyl. The term "arylene" refers to a bivalent 6-carbon monocyclic, 10-carbon bicyclic, 14-carbon tricyclic aromatic ring system. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, aryl, arylene, heteroaryl, and heteroarylene mentioned above include both substituted and unsubstituted moieties. Examples of substituents include, but are not limited to, halo, hydroxy, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl. Cycloalkyl, heterocycloalkyl, aryl, and heteroaryl may also include fused moieties, such as cycloalkyl, heterocycloalkyl, aryl, or heteroaryl. For example, aryl can be

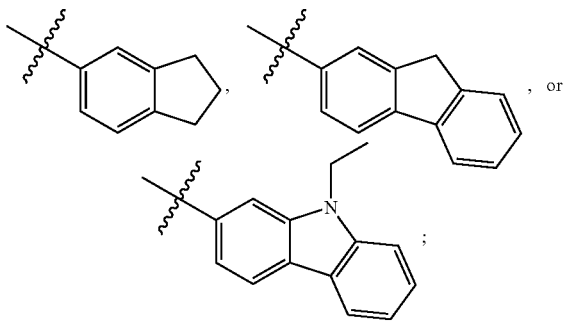

cycloalkyl can be

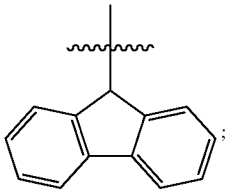

and cycloheteroalkyl can be

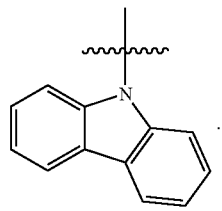

Shown in the table below are 80 exemplary compounds of this invention:

| Compound No. | Structure | Name |
|---|---|---|
| 1 | ![structure] | 1-naphthalen-1-yl-3-[5-(3-thioureido-phenoxy)-pentyl]-thiourea |
| 2 | ![structure] | 1-naphthalen-1-yl-3-[5-(3-thioureido-phenoxy)-pentyl]-urea |
| 3 | ![structure] | 1-naphthalen-1-yl-3-[5-(4-thioureido-phenoxy)-pentyl]-thiourea |

-continued

| Compound No. | Structure | Name |
|---|---|---|
| 4 | 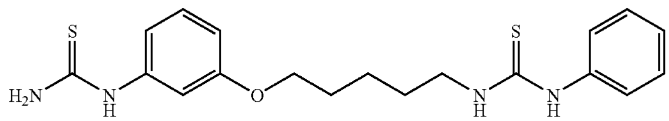 | 1-phenyl-3-[5-(3-thioureido-phenoxy)-pentyl]-thiourea |
| 5 | 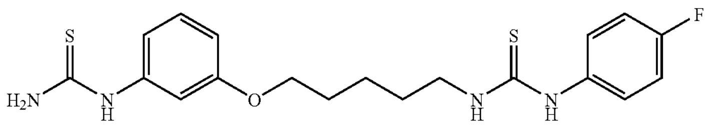 | 1-(4-fluorophenyl)-3-[5-(4-thioureido-phenoxy)-pentyl]-thiourea |
| 6 | 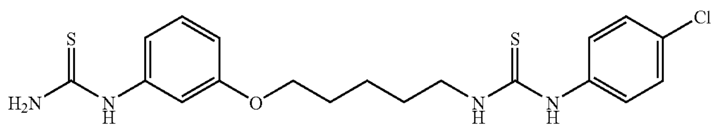 | 1-(4-chlorophenyl)-3-[5-(3-thioureido-phenoxy)-pentyl]-thiourea |
| 7 | 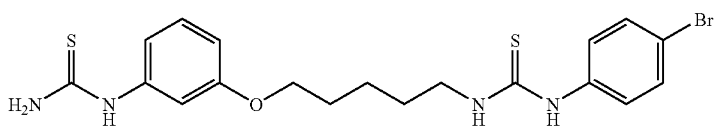 | 1-(4-bromophenyl)-3-[5-(3-thioureido-phenoxy)-pentyl]-thiourea |
| 8 | 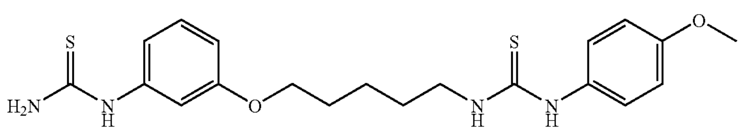 | 1-(4-methoxyphenyl)-3-[5-(3-thioureido-phenoxy)-pentyl]-thiourea |
| 9 | 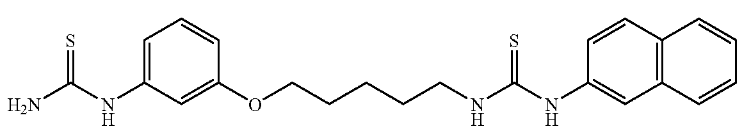 | 1-naphthalen-2-yl-3-[5-(3-thioureido-phenoxy)-pentyl]-thiourea |
| 10 | 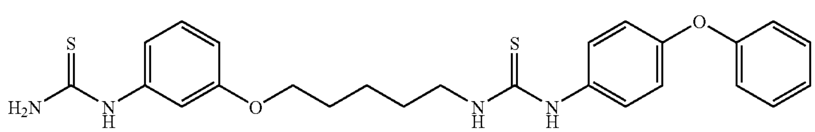 | 1-(4-phenoxyphenyl)-3-[5-(3-thioureido-phenoxy)-pentyl]-thiourea |
| 11 | 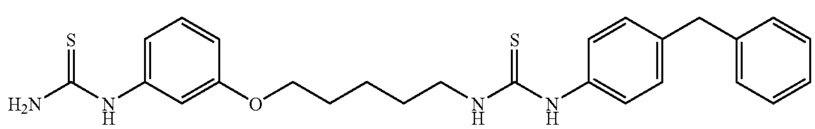 | 1-(4-benzylphenyl)-3-[5-(3-thioureido-phenoxy)-pentyl]-thiourea |
| 12 | 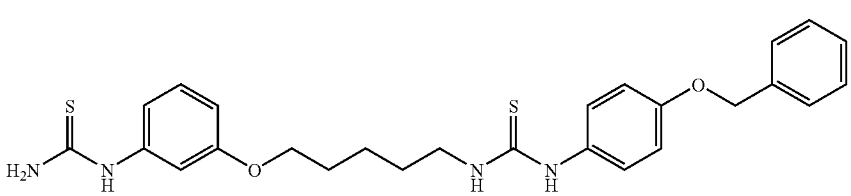 | 1-(4-benzyloxyphenyl)-3-[5-(3-thioureido-phenoxy)-pentyl]-thiourea |
| 13 | 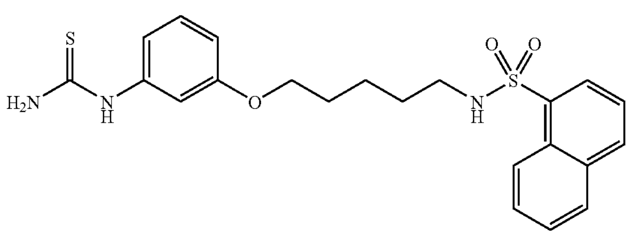 | naphthalene-1-sulfonic acid [5-(3-thioureido-phenoxy)-pentyl]-amide |

| Compound No. | Structure | Name |
|---|---|---|
| 14 | 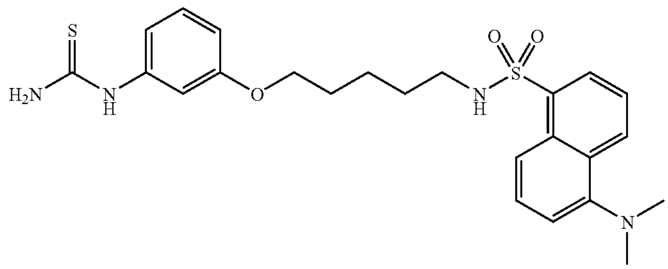 | 5-dimethylamino-naphthalene-1-sulfonic acid [5-(3-thioureido-phenoxy)-pentyl]-amide |
| 15 | 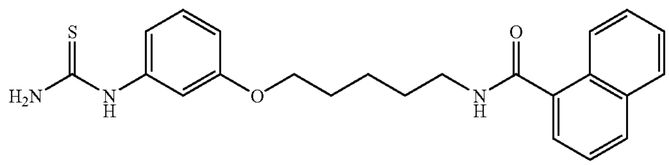 | naphthalene-1-carboxylic acid [5-(3-thioureido-phenoxy)-pentyl]-amide |
| 16 | 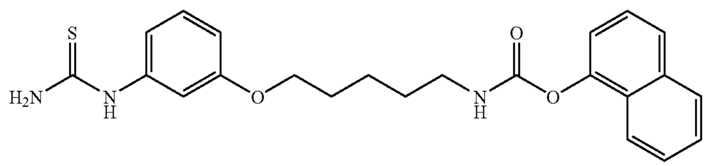 | [5-(3-thioureido-phenoxy)-pentyl]-carbamic acid naphthalen-1-yl ester |
| 17 | 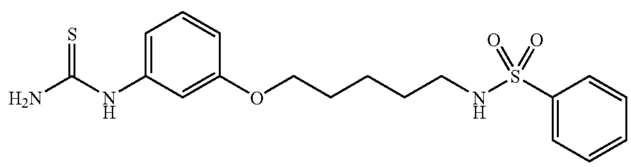 | N-[5-(3-thioureido-phenoxy)-pentyl]-benzenesulfonamide |
| 18 | 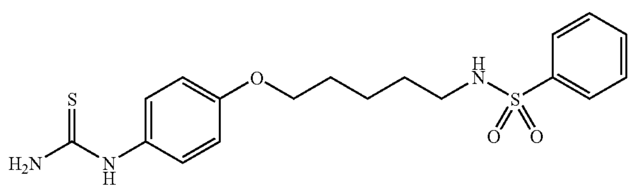 | N-[5-(3-thioureido-phenoxy)-pentyl]-benzenesulfonamide |
| 19 | 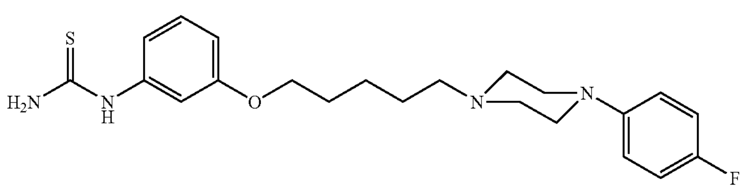 | (3-{5-[4-(4-fluoro-phenyl)-piperazin-1-yl]-pentyloxy}-phenyl)-thiourea |
| 20 | 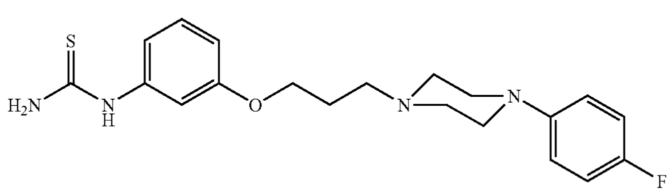 | (3-{3-[4-(4-fluoro-phenyl)-piperazin-1-yl]-propoxy}-phenyl)-thiourea |
| 21 | 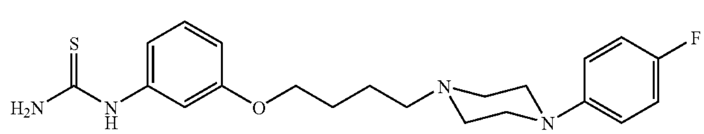 | (3-{4-[4-(4-fluoro-phenyl)-piperazin-1-yl]-butoxy}-phenyl)-thiourea |

-continued

| Compound No. | Structure | Name |
|---|---|---|
| 22 | 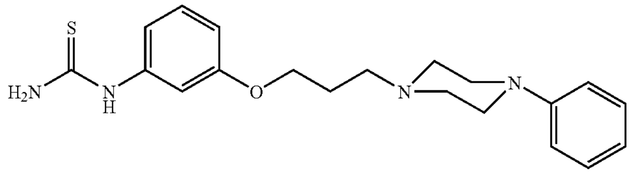 | {3-[3-(4-phenyl-piperazin-1-yl)-propoxy]-phenyl}-thiourea |
| 23 | 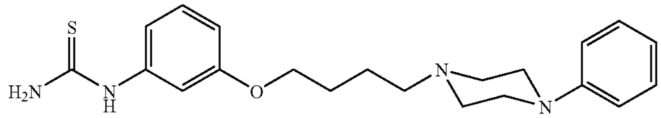 | {3-[4-(4-phenyl-piperazin-1-yl)-butoxy]-phenyl}-thiourea |
| 24 | 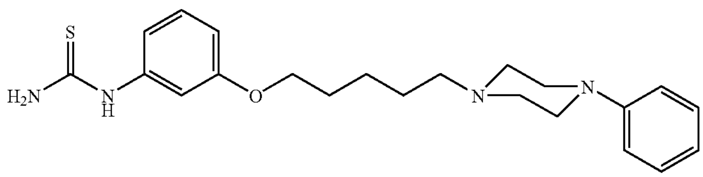 | {3-[5-(4-phenyl-piperazin-1-yl)-pentyloxy]-phenyl}-thiourea |
| 25 | 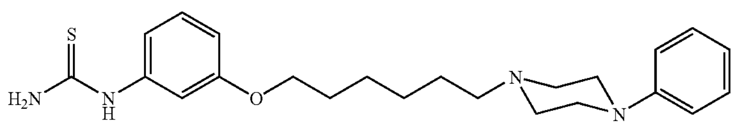 | {3-[6-(4-phenyl-piperazin-1-yl)-hexyloxy]-phenyl}-thiourea |
| 26 | 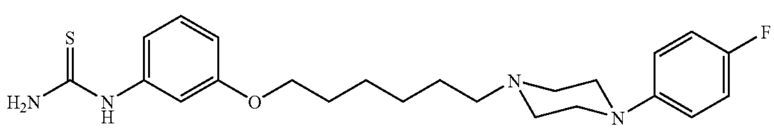 | {3-[6-[4-(4-fluoro-phenyl)-piperazin-1-yl]-hexyloxy}-phenyl)-thiourea |
| 27 | 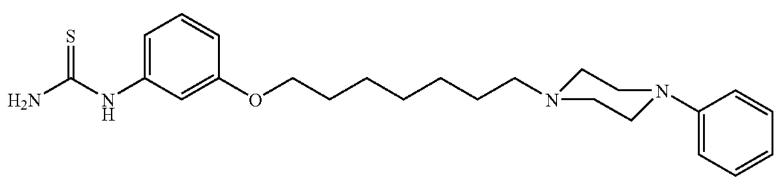 | {3-[7-(4-phenyl-piperazin-1-yl)-heptyloxy]-phenyl}-thiourea |
| 28 | 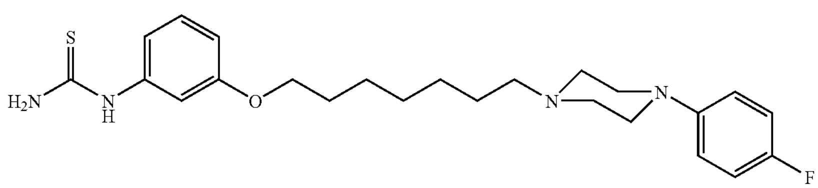 | (3-{7-[4-(4-fluoro-phenyl)-piperazin-1-yl]-heptyloxy}-phenyl)-thiourea |
| 29 | 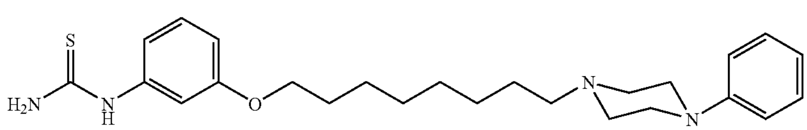 | {3-[8-(4-phenyl-piperazin-1-yl)-octyloxy]-phenyl}-thiourea |
| 30 | 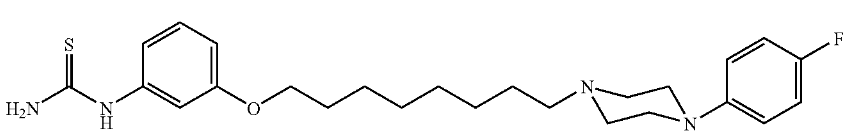 | (3-{8-[4-(4-fluoro-phenyl)-piperazin-1-yl]-octyloxy}-phenyl)-thiourea |

-continued

| Compound No. | Structure | Name |
|---|---|---|
| 31 | 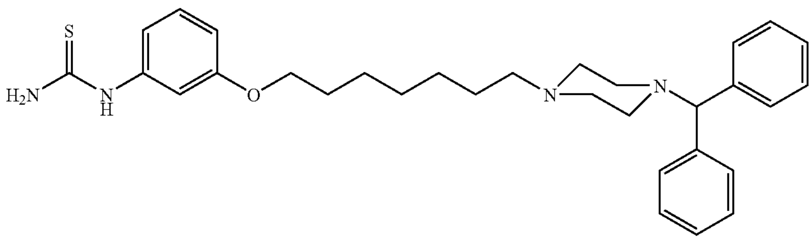 | {3-[7-(4-benzhydryl-piperazin-1-yl)-heptyloxy]-phenyl}-thiourea |
| 32 | 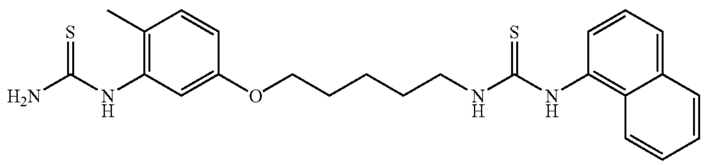 | 1-(naphthalen-1-yl)-3-(5-(3-thioureido-p-tolyloxy)pentyl)thiourea |
| 33 | 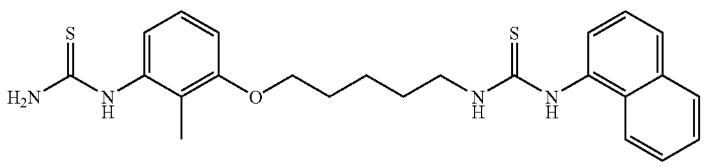 | 1-(naphthalen-1-yl)-3-(5-(3-thioureido-o-tolyloxy)pentyl)thiourea |
| 34 | 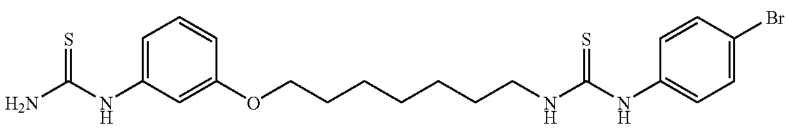 | 1-(4-bromophenyl)-3-(7-(3-thioureido)phenoxyheptyl)thiourea |
| 35 | 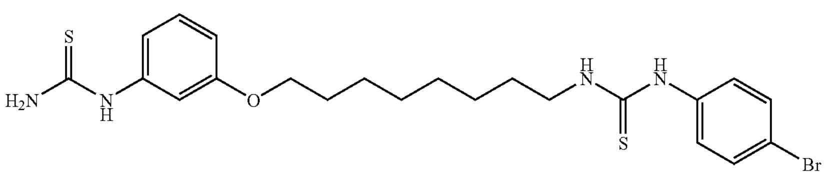 | 1-(4-bromophenyl)-3-(8-(3-thioureido phenoxy)octyl)thiourea |
| 36 | 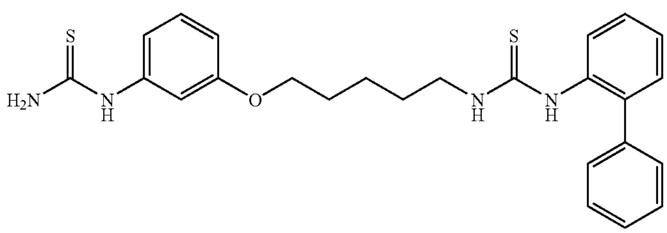 | 1-(5-(3-thioureido phenoxy)pentyl)-3-(biphenyl-2-yl)thiourea |
| 37 | 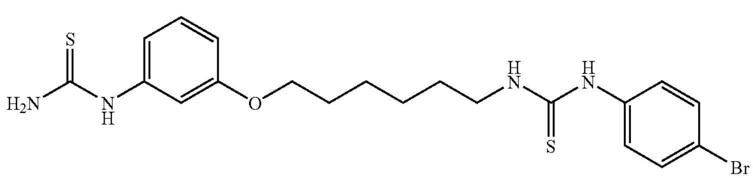 | 1-(6-(3-thioureido phenoxy)hexyl)-3-(4-bromophenyl)thiourea |
| 38 | 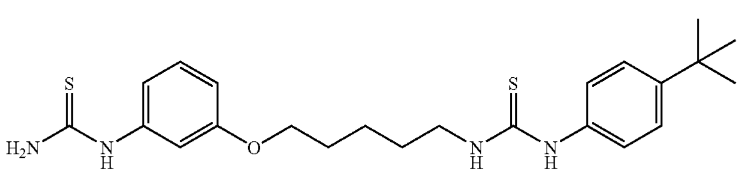 | 1-(5-(3-thioureido phenoxy)pentyl)-3-(4-tert-butylphenyl)thiourea |

-continued

| Compound No. | Structure | Name |
|---|---|---|
| 39 | 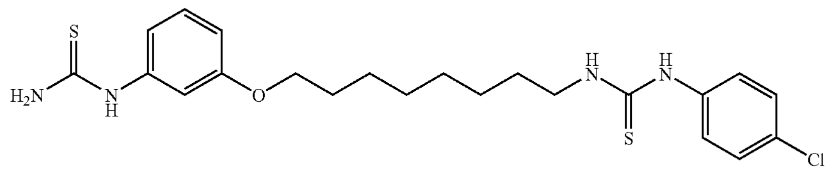 | 1-(8-(3-thioureido phenoxy)octyl)-3-(4-chlorophenyl)thiourea |
| 40 | 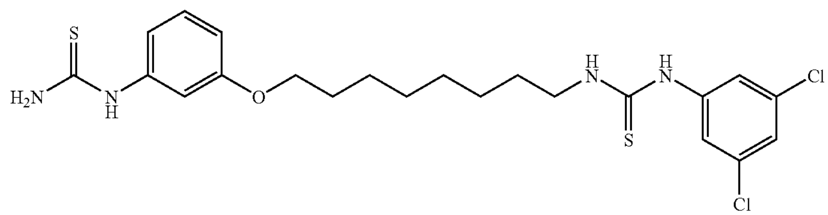 | 1-(8-(3-thioureido phenoxy)octyl)-3-(3,5-dichlorophenyl)thiourea |
| 41 | 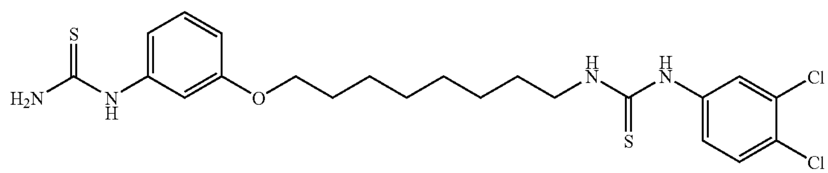 | 1-(8-(3-thioureido phenoxy)octyl)-3-(3,4-dichlorophenyl)thiourea |
| 42 | 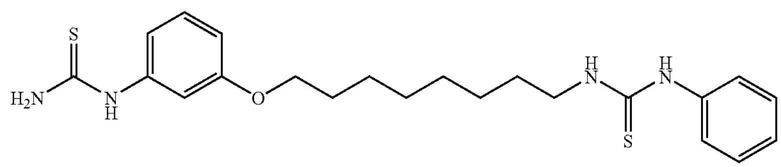 | 1-(8-(3-thioureido phenoxy)octyl)-3-phenylthiourea |
| 43 | 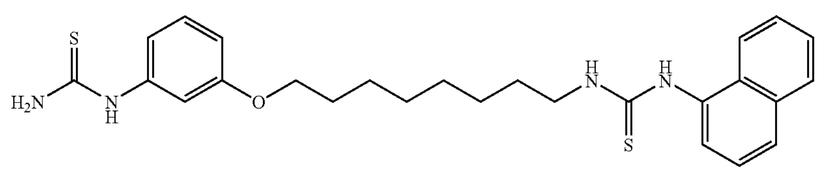 | 1-(8-(3-thioureido phenoxy)octyl)-3-(napthalen-1-yl)thiourea |
| 44 | 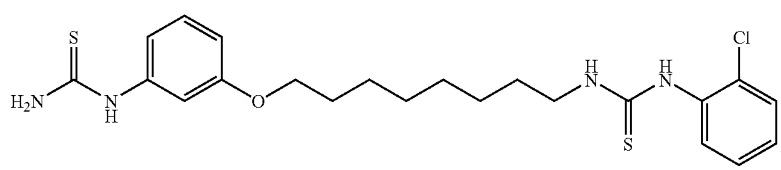 | 1-(8-(3-thioureido phenoxy)octyl)-3-(2-chlorophenyl)thiourea |
| 45 | 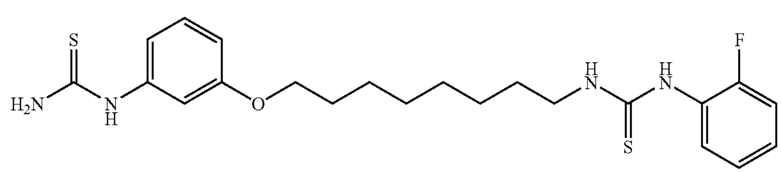 | 1-(8-(3-thioureido phenoxy)octyl)-3-(2-fluorophenyl)thiourea |
| 46 | 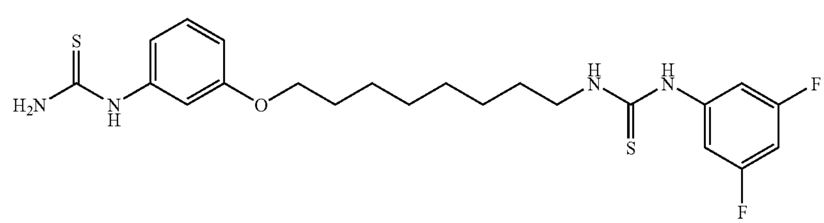 | 1-(8-(3-thioureido phenoxy)octyl)-3-(3,5-difluorophenyl)thiourea |

-continued

| Compound No. | Structure | Name |
|---|---|---|
| 47 | 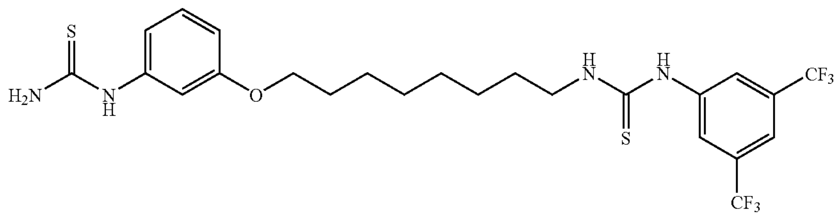 | 1-(8-(3-thioureido phenoxy)octyl)-3-(3,5-bis(trifluoromethyl)phenyl)thiourea |
| 48 | 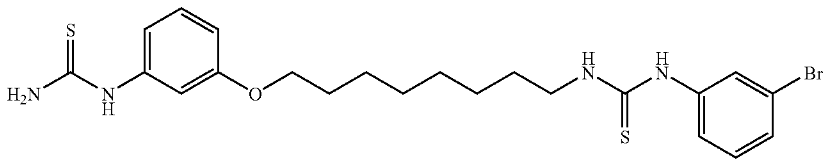 | 1-(8-(3-thioureido phenoxy)octyl)-3-(3-bromophenyl)thiourea |
| 49 | 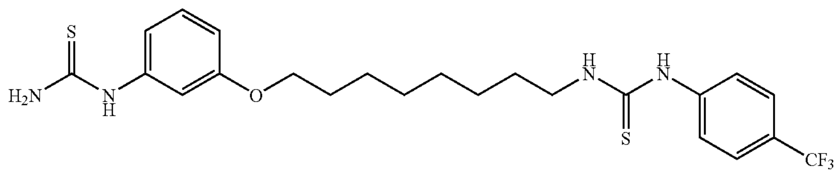 | 1-(8-(3-thioureido phenoxy)octyl)-3-(4-(trifluoromethyl)phenyl)thiourea |
| 50 | 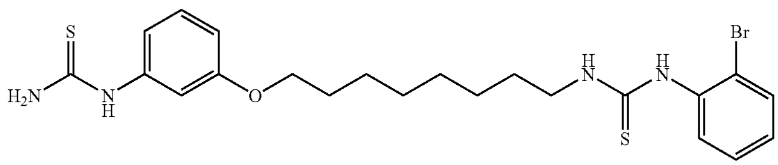 | 1-(8-(3-thioureido phenoxy)octyl)-3-(2-bromophenyl)thiourea |
| 51 | 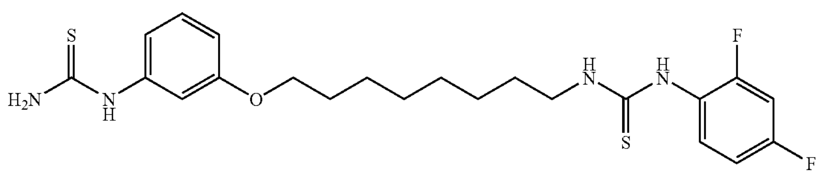 | 1-(8-(3-thioureido phenoxy)octyl)-3-(2,4-difluorophenyl)thiourea |
| 52 | 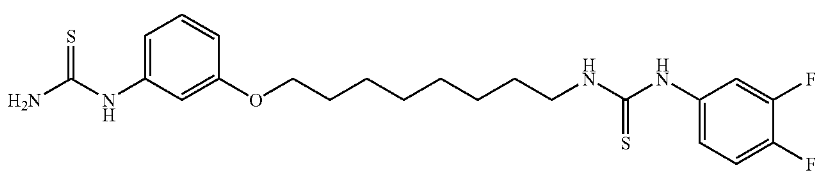 | 1-(8-(3-thioureido phenoxy)octyl)-3-(3,4-difluorophenyl)thiourea |
| 53 | 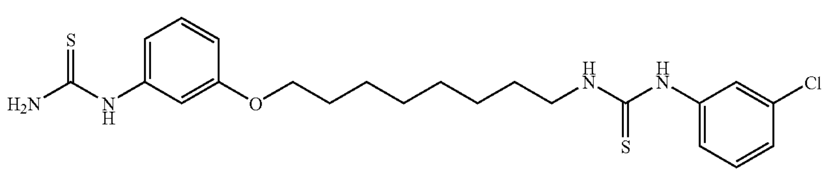 | 1-(8-(3-thioureido phenoxy)octyl)-3-(3-chlorophenyl)thiourea |
| 54 | 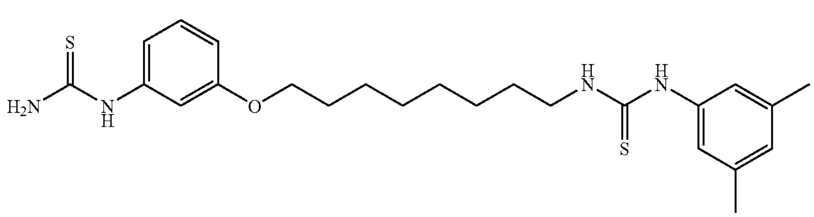 | 1-(8-(3-thioureido phenoxy)octyl)-3-(3,5-dimethylphenyl)thiourea |

-continued

| Compound No. | Structure | Name |
|---|---|---|
| 55 | 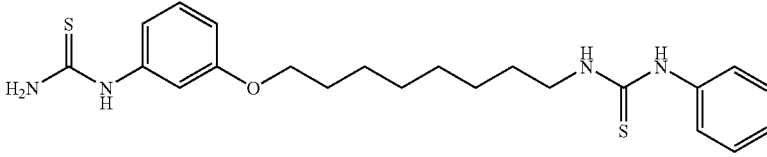 | 1-(8-(3-thioureido phenoxy)octyl)-3-(3-(trifluoromethyl)phenyl) thiourea |
| 56 | 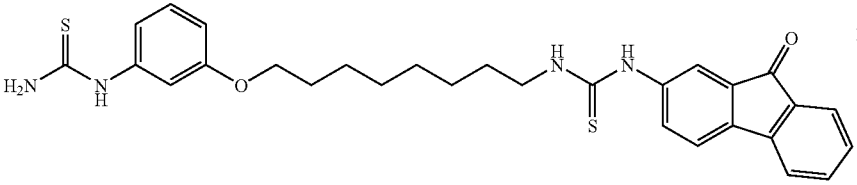 | 1-(8-(3-thioureido phenoxy)octyl)-3-(9-oxo-9H-fluoren-2-yl)thiourea |
| 57 | 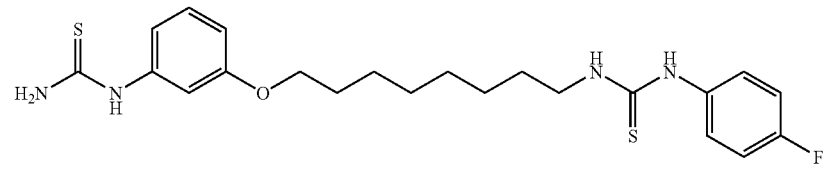 | 1-(8-(3-thioureido phenoxy)octyl)-3-(4-fluorophenyl)thiourea |
| 58 | 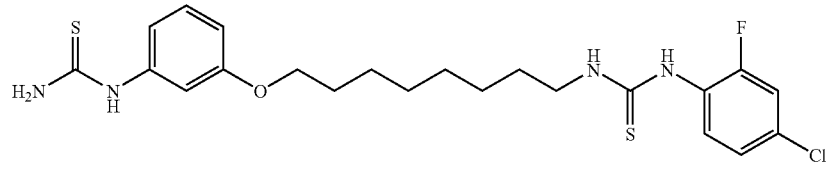 | 1-(8-(3-thioureido phenoxy)octyl)-3-(4-chloro-2-fluorophenyl)thiourea |
| 59 | 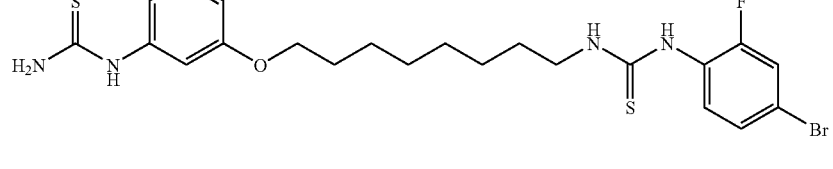 | 1-(8-(3-thioureido phenoxy)octyl)-3-(4-bromo-2-fluorophenyl)thiourea |
| 60 | 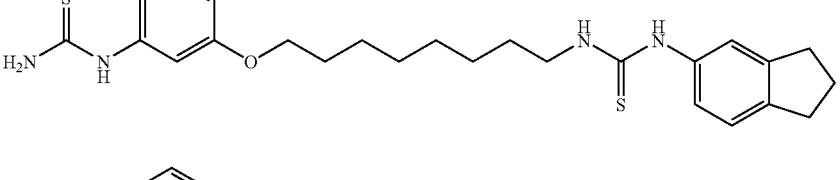 | 1-(8-(3-thioureido phenoxy)octyl)-3-(2,3-dihydro-1H-inden-5-yl)thiourea |
| 61 | 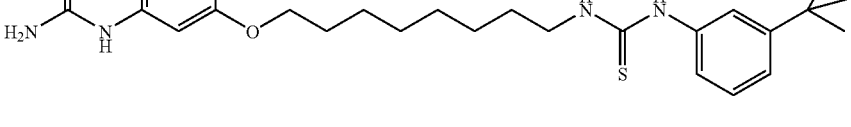 | 1-(8-(3-thioureido phenoxy)octyl)-3-(3-tert-butylphenyl)thiourea |
| 62 | 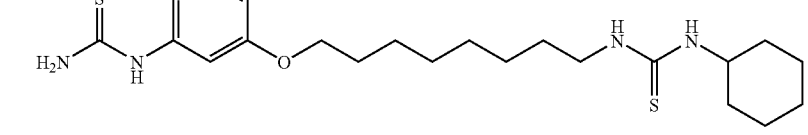 | 1-(8-(3-thioureido phenoxy)octyl)-3-cyclohexylthiourea |

-continued

| Compound No. | Structure | Name |
|---|---|---|
| 63 | 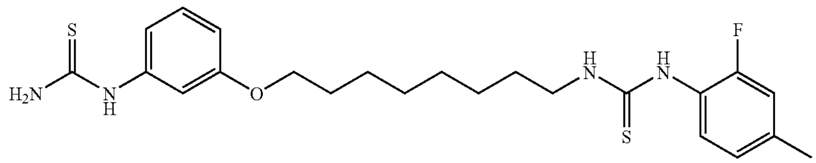 | 1-(8-(3-thioureido phenoxy)octyl)-3-(2-fluoro-4-methylphenyl)thiourea |
| 64 | 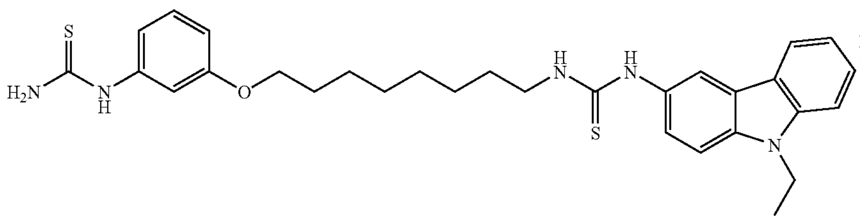 | 1-(8-(3-thioureido phenoxy)octyl)-3-(9-ethyl-9H-carbazol-3-yl)thiourea |
| 65 | 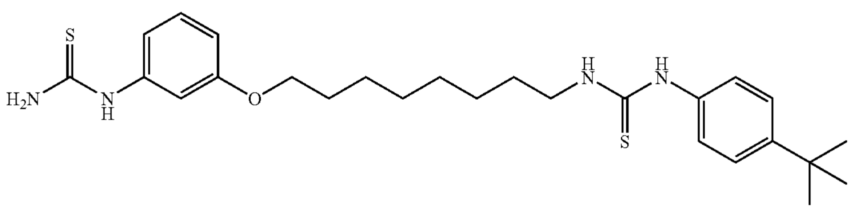 | 1-(8-(3-thioureido phenoxy)octyl)-3-(4-tert-butylphenyl)thiourea |
| 66 | 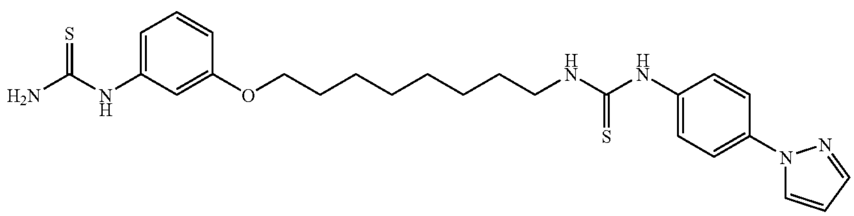 | 1-(4-(1H-pyrazol-1-yl)phenyl)-3-(8-(3-thioureido phenoxy)octyl)thiourea |
| 67 | 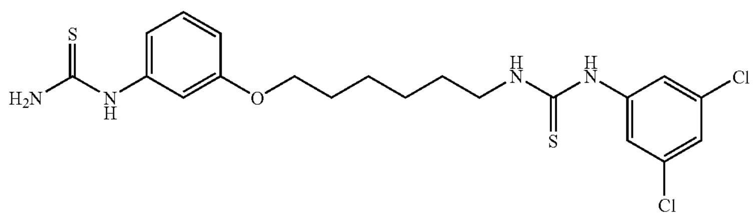 | 1-(6-(3-thioureido phenoxy)hexyl)-3-(3,5-dichlorophenyl)thiourea |
| 68 | 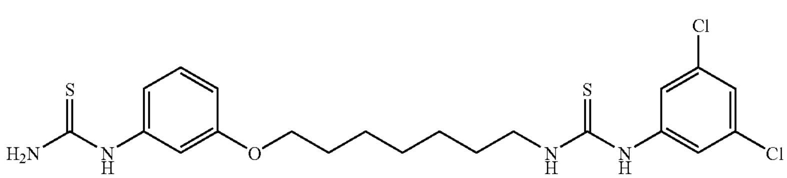 | 1-(7-(3-thioureido phenoxy)heptyl)-3-(3,5-dichlorophenyl)thiourea |
| 69 | 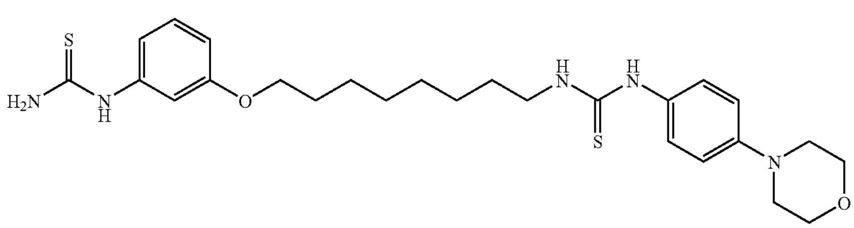 | 1-(8-(3-thioureido phenoxy)octyl)-3-(4-morpholinophenyl)thiourea |

-continued

| Compound No. | Structure | Name |
|---|---|---|
| 70 | 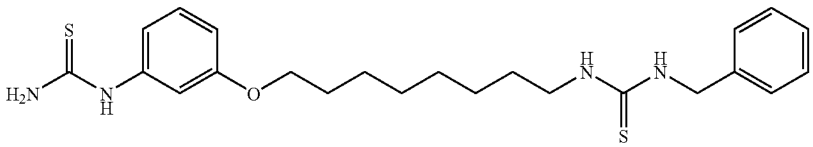 | 1-(8-(3-thioureido phenoxy)octyl)-3-benzylthiourea |
| 71 | 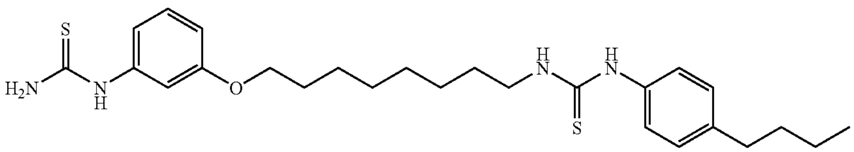 | 1-(8-(3-thioureido phenoxy)octyl)-3-(4-butylphenyl)thiourea |
| 72 | 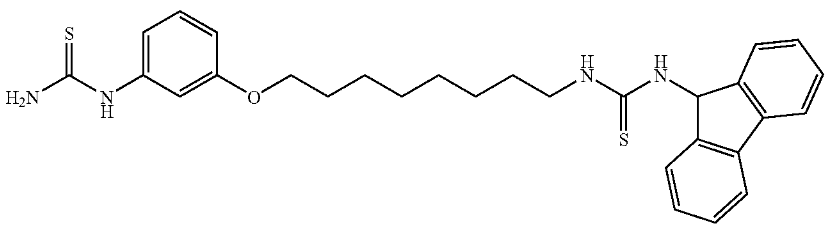 | 1-(8-(3-thioureido phenxoy)octyl)-3-(9H-fluoren-9-yl)thiourea |
| 73 | 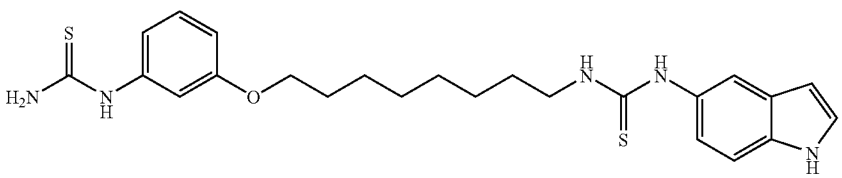 | 1-(8-(3-thioureido phenoxy)octyl)-3-(1H-indol-5-yl)thiourea |
| 74 | 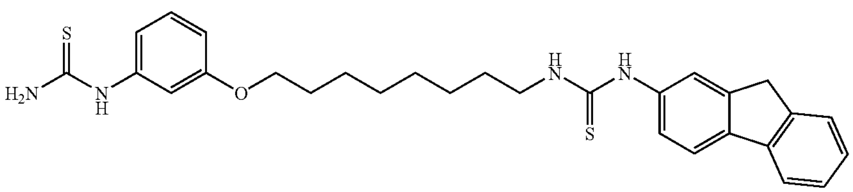 | 1-(8-(3-thioureido phenoxy)octyl)-3-(9H-fluoren-2-yl)thiourea |
| 75 | 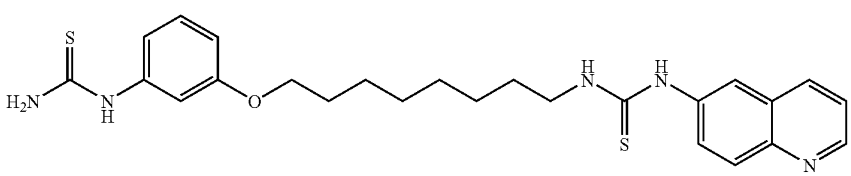 | 1-(8-(3-thioureido phenoxy)octyl)-3-(quinolin-6-yl)thiourea |
| 76 | 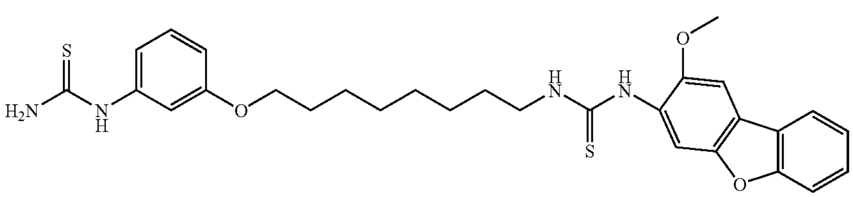 | 1-(8-(3-thioureido phenoxy)octyl)-3-(2-methoxydibenzo[b,d]furan-3-yl)thiourea |
| 77 | 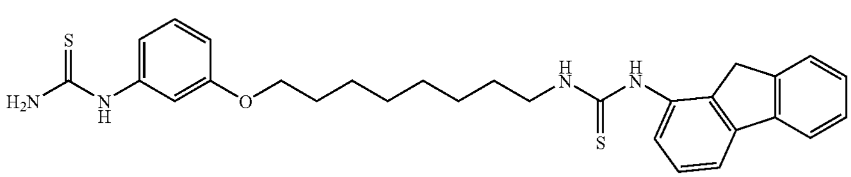 | 1-(8-(3-thioureido phenoxy)octyl)-3-(9H-fluoren-1-yl)-thiourea |

-continued

| Compound No. | Structure | Name |
|---|---|---|
| 78 | 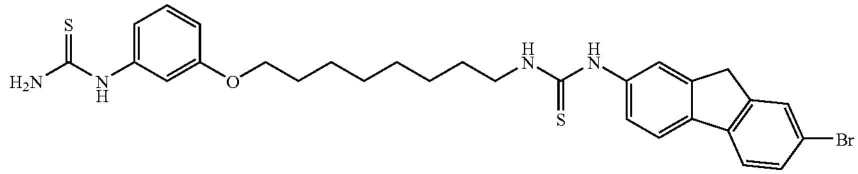 | 1-(8-(3-thioureido phenoxy)octyl)-3-(7-bromo-9H-fluoren-2-yl)-thiourea |
| 79 | 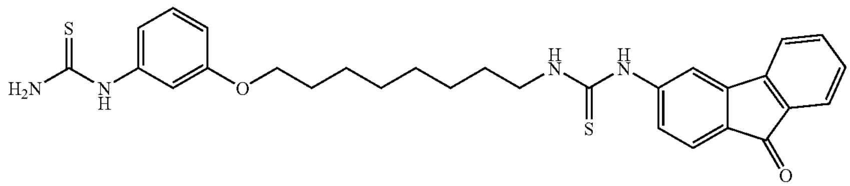 | 1-(8-(3-thioureido phenoxy)octyl)-3-(9-oxo-9H-fluoren-3-yl)thiourea |
| 80 | 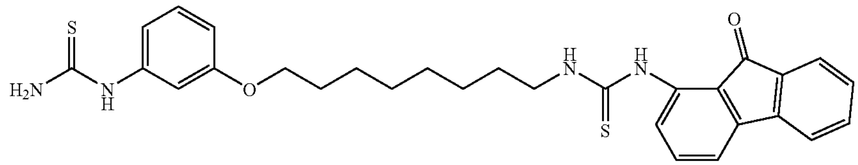 | 1-(8-(3-thioureido phenoxy)octyl)-3-(9-oxo-9H-fluoren-1-yl)thiourea |

In still another aspect, this invention relates to a method of treating HCV infection by administering to a subject infected with HCV an effective amount of one or more of the thiourea compounds described above.

Also within the scope of this invention is a pharmaceutical composition containing one or more of the above-described thiourea compounds for use in treating HCV infection, as well as this therapeutic use and use of the compounds for the manufacture of a medicament for treating HCV infection.

The details of one or more embodiments of the invention are set forth in the description below. Other features, objects, and advantages of the invention will be apparent from the description and drawings, and from the claims.

DETAILED DESCRIPTION

The thiourea compounds of this invention can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-3 below show transformations for synthesizing compounds of this invention ($A_1$ and $A_2$ defined above).

The route shown in Scheme 1 exemplifies synthesis of the thiourea compounds of this invention in which Z is NHC(=O)NH or NH(C=S)NH (see formula I above); O and S are both denoted as W in this scheme. Dibromo alkyl i is reacted with a nitro- and hydroxy-substituted aryl or heteroaryl (e.g., 3-nitrophenol) in the presence of potassium carbonate in N-methylpyrrolidone (NMP) to form an alkoxy-containing compound ii, which is subsequently treated with sodium azide to afford azide compound iii. Reduction of the azide compound leads to amine compound iv, which is then coupled with aryl isocyanate (or isothiocyanate) to form a urea (or thiourea) intermediate v. Subsequent reduction of the nitro group produces amine compound vi, which is then reacted with thiocarbonyl diimidazole (TCDI), followed by treatment with 25% aqueous ammonia solution, to afford thiourea compound vii.

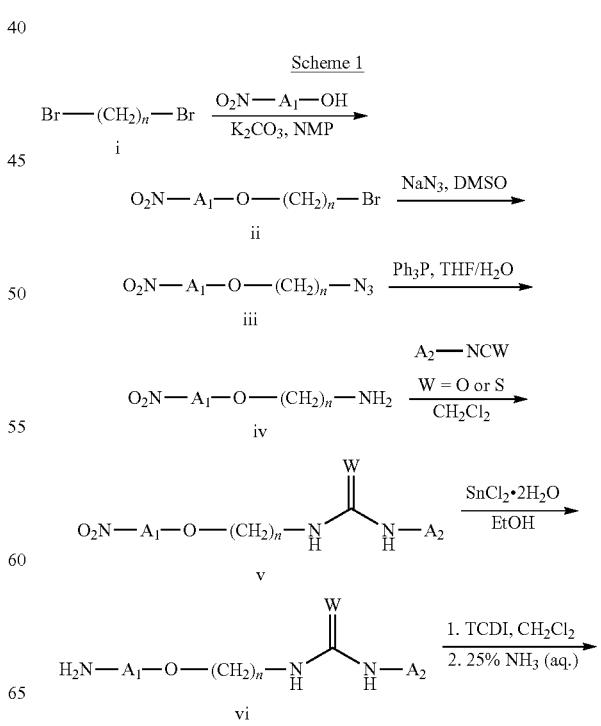

Scheme 1

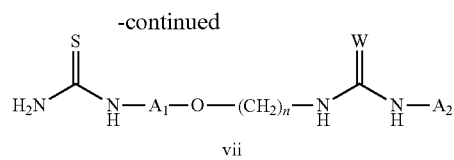

The route shown in Scheme 2 exemplifies synthesis of the thiourea compounds of this invention in which Z is —NHSO$_2$—, —NHC(=O)—, or —NHC(=O)O— (see formula I above). Amine compound iv is coupled with acyl chloride (sulfonyl chloride, or chloroformate) to provide compound viii. Reduction of compound viii with SnCl$_2$ produces amine compound ix, which is subsequently reacted with TCDI to afford thiourea compound x.

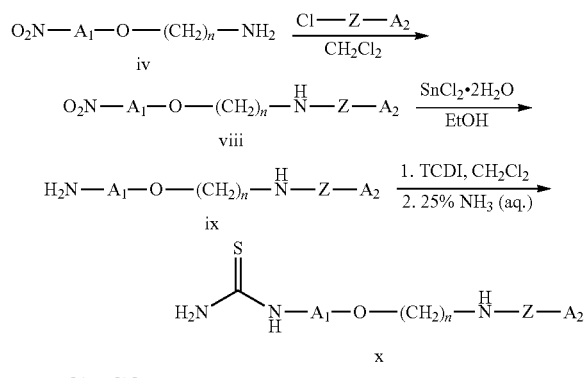

The route shown in Scheme 3 exemplifies synthesis of the thiourea compounds of this invention in which Z is piperazinyl (see formula I above). Coupling bromo compound ii with piperazine derivative affords compound xi, which is subsequently converted to amine xii by reducing its nitro group. Amine xii compound is then reacted with TCDI to afford thiourea compound x.

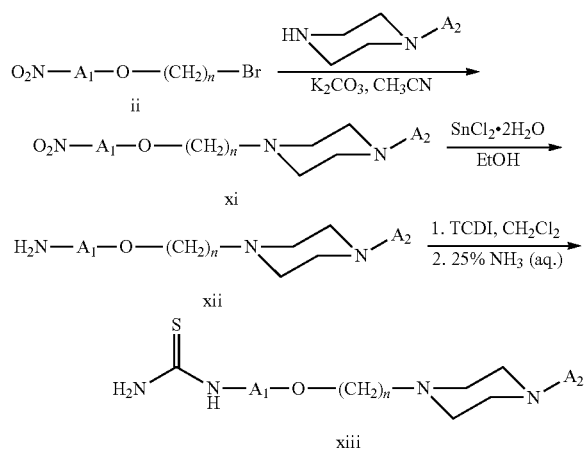

A thiourea compound thus synthesized can be further purified by flash column chromatography, high performance liquid chromatography, crystallization, or any other suitable methods.

Also within the scope of this invention are (1) a pharmaceutical composition that contains an effective amount of at least one of the thiourea compounds of this invention and a pharmaceutically acceptable carrier, and (2) a method for treating HCV infection by administering to a subject in need of this treatment an effective amount of such a thiourea compound.

As used herein, the term "treating" refers to administering a thiourea compound to a subject that has HCV infection, or has a symptom of HCV infection, or has a predisposition toward HCV infection, with the purpose to prevent, cure, heal, alleviate, relieve, alter, remedy, ameliorate, improve, or affect the HCV infection, the symptoms of the HCV infection, or the predisposition toward the HCV infection. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A thiourea compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the thiourea compounds, or more solubilizing agents, can be utilized as pharmaceutical carriers for delivery of the oxadiazole compounds. Examples of other carriers include colloidal silicon dioxide, magnesium stearate, sodium lauryl sulfate, and D&C Yellow #10.

Suitable in vitro assays can be used to preliminarily evaluate the efficacy of the thiourea compounds of this invention in inhibiting HCV replication. The compounds can further be examined for their efficacy in treating HCV infection. For example, a compound can be administered to an animal (e.g., a mouse model) infected with HCV and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Synthesis of 1-naphthalen-1-yl-3-[5-(3-thioureido-phenoxy) -pentyl]-thiourea (Compound 1)

To a stirred solution of 3-nitrophenol (4.17 g, 30.0 mmol) and 1,5-dibromo-pentane (7.59 g, 33.0 mmol) in N-methylpyrrolidinone (100 mL) was added potassium carbonate (6.21 g, 45.0 mmol), and the resulting mixture was stirred at 90° C. for 6 hours. The reaction mixture was quenched with water (30 mL) followed by extraction with ethyl acetate (30 mL×3). The combined organic layers were washed with brine and then concentrated under vacuum. The residue was purified by silica gel column chromatography to give 1-(5-bromo-pentyloxy)-3-nitro-benzene (5.10 g, 17.7 mmol, 59%) as a yellow liquid.

The resulting yellow liquid (3.60 g, 12.5 mmol) was dissolved in DMSO (20 mL). Sodium azide (1.22 g, 18.7 mmol) was slowly added. The reaction mixture was stirred overnight at room temperature and then quenched with water (30 mL) followed by extraction with ether (30 mL×3). The combined organic layers were washed with brine and then concentrated under vacuum. The residue was purified by silica gel column chromatography to give 1-(5-azido-pentyloxy)-3-nitro-benzene (3.12 g, 12.5 mmol, 99%) as a yellow liquid.

To a solution of 1-(5-azido-pentyloxy)-3-nitro-benzene (3.12 g, 12.5 mmol) in 50 mL THF and 1 mL $H_2O$ was added triphenylphosphine (3.27 g, 12.5 mmol). The reaction mixture was stirred at room temperature for 48 hours and then was partitioned with ethyl acetate and water. The aqueous solution was extracted with ethyl acetate (3×50 mL). The combined organic phases were washed with brine, dried over $MgSO_4$, and concentrated to give a yellow liquid, which was purified by silica gel column chromatography to give 5-(3-nitro-phenoxy)-pentylamine (2.75 g, 12.3 mmol, 98%) as a yellow liquid.

To a solution of 5-(3-nitro-phenoxy)-pentylamine (867 mg, 3.87 mmol) in dichloromethane (5 mL) was added 1-naphthyl isothiocyanate (788 mg, 4.26 mmol) at room temperature. The reaction mixture was stirred at room temperature overnight. After removal of the solvent, the residue was purified by silica gel column chromatography to give 1-naphthalen-1-yl-3-[5-(3-nitro-phenoxy) -pentyl]-thiourea (1.3 g, 3.18 mmol, 82%) as a yellow gel.

The yellow gel (1.3 g, 3.18 mmol) was dissolved in 30 ml ethanol. To this solution was added Tin (II) chloride dihydrate (4.05 g, 15.9 mmol). The reaction mixture was stirred at 70° C. for 6 hours. Upon cooling, saturated aqueous sodium bicarbonate solution was added to adjust the pH value to 7. The solution was then extracted with ethyl acetate (3×50 mL). The combined organic phases were washed with brine, dried over $MgSO_4$, and concentrated to give a yellow gel, which was purified by silica gel column chromatography eluting with ethyl acetate and n-hexane to give 1-[5-(3-amino-phenoxy)-pentyl]-3-naphthalen-1-yl-thiourea (1.2 g, 3.17 mmol, 99%) as a light yellow solid.

1-[5-(3-amino-phenoxy)-pentyl]-3-naphthalen-1-yl-thiourea (1.76 g, 4.65 mmol) was mixed with thiocarbonyl diimidazole (993 mg, 5.58 mmol) in dichloromethane (25 mL) and was stirred at room temperature for 2 hours. 25% aqueous ammonia solution (3 mL) was added and the reaction mixture was stirred at room temperature overnight. After removal of the solvent, the residue was purified by silica gel column chromatography eluting with ethyl acetate and n-hexane to give Compound 1 (1.7 g, 3.88 mmol, 83%) as a white solid. MS (EI): m/z 439 (M+H).

EXAMPLES 2-12

Synthesis of Compounds 2-12

Compounds 2-12 were prepared in a manner similar to that described in Example 1.

EXAMPLE 13

Synthesis of naphthalene-1-sulfonic acid [5-(3-thioureido-phenoxy) -pentyl]-amide (Compound 13)

To a stirred solution of 5-(3-nitro-phenoxy)-pentylamine (336 mg, 1.5 mmol) and naphthalene-1-sulfonyl chloride (340 mg, 1.5 mmol) in dichloromethane (10 mL) was added triethylamine (182 mg, 1.8 mmol), and the resulting mixture was stirred at room temperature overnight. The reaction mixture was quenched with saturated ammonium chloride (30 mL) followed by extraction with ethyl acetate (10 mL×3). The organic layers were combined, washed with brine, and then concentrated under vacuum. The residue was subjected to column chromatography on silica gel to give naphthalene-1-sulfonic acid [5-(3-nitro-phenoxy)-pentyl]-amide (600 mg, 1.45 mmol, 97%) as a yellow liquid.

The yellow liquid was dissolved in 10 ml ethanol. To this solution was added Tin (II) chloride dihydrate (1.85 g, 7.25 mmol). The reaction mixture was stirred at 70° C. for 6 hours. After cooling, saturated aqueous sodium bicarbonate solution was added adjust the pH value to 7. The solution was extracted with ethyl acetate (30 mL×3), and the combined organic phases were washed with brine, dried over $MgSO_4$, and concentrated to give a yellow liquid, which was purified by silica gel column chromatography eluting with ethyl acetate and n-hexane to give naphthalene-1-sulfonic acid [5-(3-amino-phenoxy)-pentyl]-amide (557 mg, 1.45 mmol, 99%) as a light yellow liquid.

A solution of the above-obtained compound (557 mg, 1.45 mmol) and thiocarbonyl diimidazole (310 mg, 1.74 mmol) in dichloromethane (5 mL) was stirred at room temperature for 2 hours. 25% aqueous ammonia solution (2 mL, excess) was added, and the reaction mixture was stirred at room temperature overnight. After removal of the solvent, the residue was purified by silica gel column chromatography eluting with ethyl acetate and n-hexane to give naphthalene-1-sulfonic acid [5-(3-thioureido-phenoxy)-pentyl]-amide (compound 13) (300 mg, 0.68 mmol, 47%) as a white solid. MS (EI): m/z 444 (M+H).

EXAMPLES 14-18

Synthesis of Compounds 14-18

Compounds 14-18 were prepared in a manner similar to that described in Example 13.

EXAMPLE 19

Synthesis of (3-{5-[4-(4-fluoro-phenyl)-piperazin-1-yl]-pentyloxy}-phenyl)-thiourea (Compound 19)

To a stirred solution of 1-(5-bromo-pentyloxy)-3-nitrobenzene (432 mg, 1.5 mmol) and 1-(4-fluoro-phenyl)-piperazine (297 mg, 1.65 mmol) in acetonitrile (5 mL) was added potassium carbonate (414 mg, 3.0 mmol). After refluxed for 6 hours, the reaction mixture was quenched with water (10 mL) followed by extraction with ethyl acetate (10 mL×3). The combined organic layers were washed with brine and then concentrated under vacuum. The resulting residue was purified by silica gel column chromatography to give 1-(4-fluoro-phenyl)-4-[5-(3-nitro -phenoxy)-pentyl]-piperazine (549 mg, 1.42 mmol, 94%) as a yellow solid.

The obtained compound (549 mg, 1.42 mmol) was dissolved in 5 ml ethanol. Tin (II) chloride dihydrate (1.81 g, 7.08 mmol) was then added. The reaction mixture was stirred at 70° C. for 3 hours. Upon cooling, saturated aqueous sodium bicarbonate solution was added to adjust the mixture's pH value to 7. The solution was extracted with ethyl acetate (3×10 mL), and the combined organic phases were washed with brine, dried over $MgSO_4$, and concentrated to give a white solid, which was purified by silica gel column chromatography eluting with ethyl acetate-n-hexane to give 3-{5-[4-(4-fluoro-phenyl)-piperazin-1-yl]-pentyloxy}-phenylamine (500 mg, 1.40 mmol, 99%) as a white solid.

A solution of 3-{5-[4-(4-fluoro-phenyl)-piperazin-1-yl]-pentyloxy}-phenylamine (500 mg, 1.40 mmol) and thiocarbonyl diimidazole (299 mg, 1.68 mmol) in dichloromethane (4 mL) was stirred at room temperature for 2 hours. 25% aqueous ammonia solution (2 mL) was added. The reaction mixture was stirred at room temperature overnight and then the solvent was removed. The residue was purified by silica gel column chromatography eluting with ethyl acetate and n-hexane to give (3-{5-[4-(4-fluoro-phenyl)-piperazin-1-yl]-pentyloxy}-phenyl)-thiourea (Compound 19) (425 mg, 1.02 mmol, 73%) as a white solid. MS (EI): m/z 417 (M+H).

EXAMPLES 20-31

Synthesis of Compounds 20-31

Each of compounds 20-31 were prepared in a manner similar to that described in Example 19.

EXAMPLES 32-80

Synthesis of Compounds 32-80

Each of compounds 32-80 were prepared in a manner similar to that described in Example 1.

EXAMPLE 81

Inhibiting HCV Replication

The inhibitory activity of compounds of this invention against HCV replication was assessed using Ava5-EG (Δ4AB)SEAP, a reporter-based cell line, according to the methods described in Lee et al., Anal. Biochem., 316:162-70 (2003) and Lee et al., J. Virol Methods, 116:27-33. Briefly, Ava5-EG(Δ4AB)SEAP cells were cultured in a medium containing 500 μg/ml G418 (geneticin) and 10 μg/ml blasticidin in a 5% $CO_2$ incubator. G418 and blasticidin were purchased from Invitrogen (Carlsbad, Calif.). The cells were seeded in a 96-well plate ($5 \times 10^3$ cells/100 μl/well) and incubated at 37° C. for 24 hours. They were then treated with a solution of a test compound in DMSO at various concentrations. After 48 hours, the culture medium in each well was replaced with a fresh medium containing the test compound at the same concentrations to remove secreted alkaline phosphatase accumulated in the culture medium, if any. The cells were cultured for additional 24 hours. The culture medium was then collected and tested for SEAP activity using a Phospha-Light assay kit (Tropix, Foster, Calif., USA).

Compounds 1-5 and 13-77 were tested in this assay. Unexpectedly, most of the test compounds showed $EC_{50}$ values (i.e., the concentration of a test compound at which 50% HCV replication is inhibited) lower than 5 μM. Some of them showed even lower $EC_{50}$ values, e.g., lower than 0.1 μM.

EXAMPLE 82

Cytotoxicity Assay

Viability of cells after treatment (see Example 32 above) was determined by the MTS assay described in Cory et al., Cancer Commun., 3:207-12 (1991). Briefly, Ava5-EG (Δ4AB)SEAP cells were treated with a test compound as described above. After 48 hours, each culture medium was replaced with a fresh medium containing the test compound at the same concentration. The cells were cultured for additional 24 hours. To each well was added 100 μl of a solution containing phenol red-free DMEM, [3-(4,5-dimethylthiozol-2-yl)-5-(3-carboxymethoxyphenyl)-2-(4-sulfophenyl)-2H-tetrazolium, inner salt] (Promega, Madison, Wis.), and phenazine methosulfate (Sigma, St. Louis, Mo.) at the ratio of 80:20:1. The cells were incubated at 37° C. for 1-4 hours in a 5% $CO_2$ incubator. The absorbance at 490 nm in each well was measured.

Compounds 1-5 and 13-77 were tested in this assay. Unexpectedly, 37 of the test compounds showed $CC_{50}$ values (i.e., the concentration of a test compound at which 50% of the cells are killed) greater than 50 μM.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

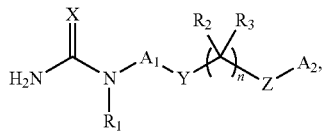

(I)

wherein
n is n is 5, 6, 7, or 8;
$R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl;
each of $R_2$ and $R_3$, independently, is H, halo, nitro, cyano, amino, hydroxy, alkoxy, aryloxy, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl;
$A_1$ is 1,3-phenylene or 1,4-phenylene;
$A_2$ is alkyl, cycloalkyl, heterocycloalkyl, aryl, or heteroaryl, in which alkyl is optionally substituted with halo, nitro, cyano, amino, hydroxy, alkoxy, aryloxy, alkylcarbonyl, alkoxycarbonyl, carboxy, aminocarbonyl, carbonylamino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl; and each of clycloalkyl, heterocycloalkyl, aryl, and heteroaryl is optionally substituted with halo, nitro, cyano, amino, hydroxy, alkoxy, aryloxy, alkylcarbonyl, alkoxycarbonyl, carboxy, aminocarbonyl, carbonylamino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl, or optionally fused with $C_3$-$C_{20}$ cycloalkyl, $C_3$-$C_{20}$ heterocycloalkyl, aryl, or heteroaryl;
X is S;
Y is O; and
Z is

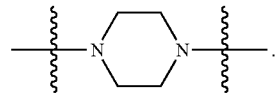

2. The compound of claim 1, wherein $A_2$ is phenyl or naphthenyl optionally substituted with halo, alkoxy, aryloxy, $C_1$-$C_{10}$ alkyl, $C_3$-$C_{20}$ cycloalkyl, aryl, or heteroaryl.

3. The compound of claim 1, wherein $A_2$ is phenyl or naphthenyl fused with $C_3$-$C_{20}$ cycloalkyl, $C_3$-$C_{20}$ heterocycloalkyl, or heteroaryl.

4. A compound of formula (I):

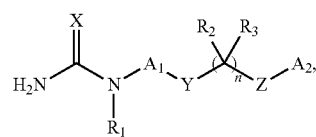

(I)

wherein
n is 1-10;
$R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl;
each of $R_2$ and $R_3$, independently, is H, halo, nitro, cyano, amino, hydroxy, alkoxy, aryloxy, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl;
$A_1$ is arylene or heteroarylene, optionally substituted with halo, nitro, cyano, amino, hydroxy, alkoxy, aryloxy, alkylcarbonyl, alkoxycarbonyl, carboxy, aminocarbonyl, carbonylamino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, aryl, or heteroaryl;
$A_2$ is phenyl or naphthenyl fused with $C_3$-$C_{20}$ cycloalkyl, $C_3$-$C_{20}$ heterocycloalkyl, or heteroaryl;
X is S;
Y is O, S, or $N(R_a)$, in which $R_a$ is H, $C_1$-$C_{10}$ alkyl, $C_3$-$C_{20}$ cycloalkyl, $C_3$-$C_{20}$ heterocycloalkyl, aryl, or heteroaryl; and
Z is $C_3$-$C_{20}$ heterocycloalkyl.

5. The compound of claim 4, wherein n is 5, 6, 7, or 8.

6. The A compound selected from the group consisting of:

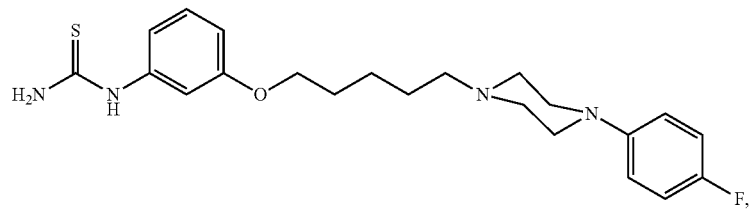

-continued
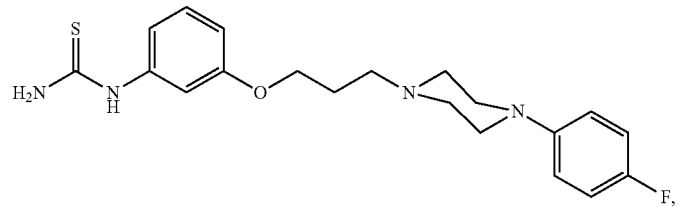
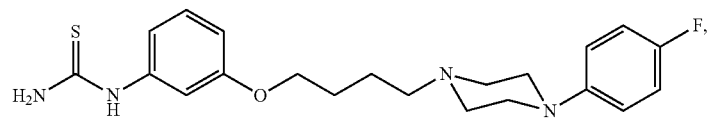
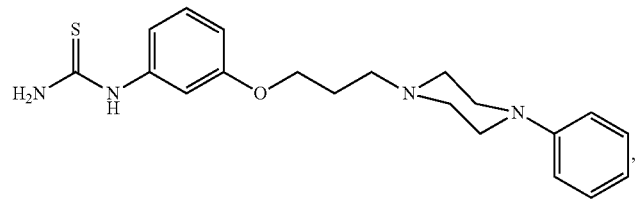
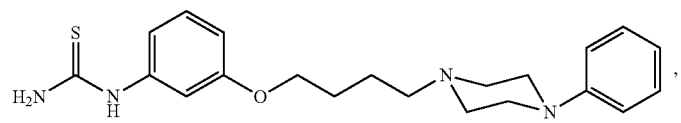
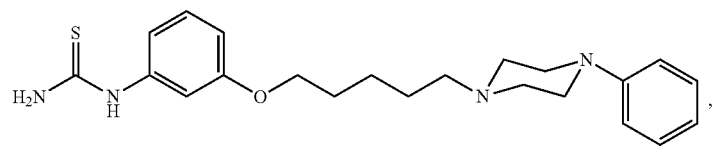
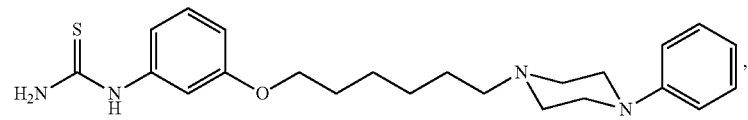
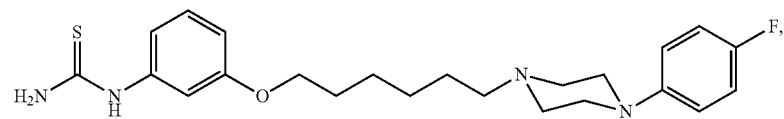
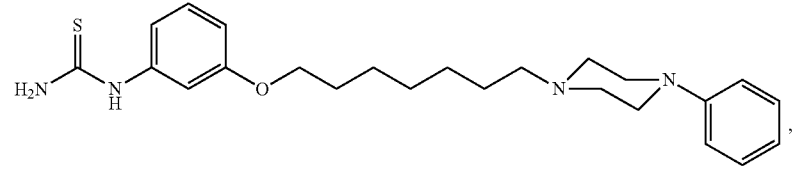
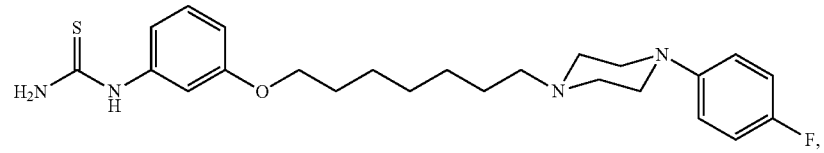
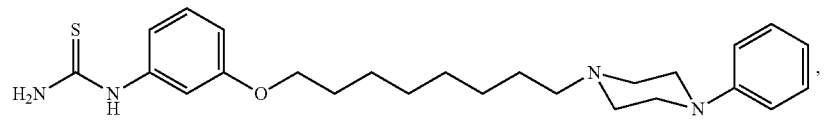

-continued
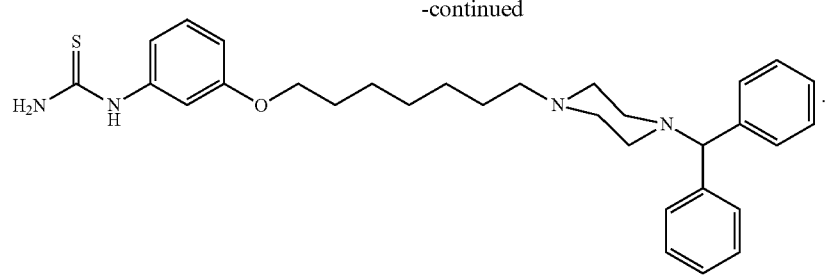
* * * * *